US005827517A

United States Patent [19]
Cook et al.

[11] Patent Number: 5,827,517
[45] Date of Patent: Oct. 27, 1998

[54] CCK ANTIBODIES USED TO IMPROVE FEED EFFICIENCY

[75] Inventors: Mark E. Cook, Madison, Wis.; Cheryl C. Miller, Dacula; Julio L. Pimentel, Buford, both of Ga.

[73] Assignee: Wisconsin Alumni Research Foundation, Madison, Wis.

[21] Appl. No.: 807,435

[22] Filed: Feb. 28, 1997

Related U.S. Application Data

[63] Continuation-in-part of Ser. No. 286,376, Aug. 5, 1994, abandoned.

[51] Int. Cl.$^6$ .................................................. A61K 39/395
[52] U.S. Cl. ..................................... 424/139.1; 424/145.1; 424/184.1; 424/185.1; 424/198.1; 530/328; 530/387.9
[58] Field of Search ........................ 514/12–16; 530/311, 530/324–328, 387.1, 387.9, 388.24, 389.2; 424/130.1, 139.1, 145.1, 184.1, 185.1, 198.1, 195.11

[56] References Cited

U.S. PATENT DOCUMENTS

| 4,748,018 | 5/1988 | Stolle et al. | 424/87 |
| 5,080,895 | 1/1992 | Tokoro | 424/85.8 |

OTHER PUBLICATIONS

Walsh et al, "Cholecystokini–Octapeptidelike Immunoreactivity in Human Plasma", Gastrenterology, vol. 82, pp. 438–444, Mar. 1982.
McLaughlin et al, "Effect of CCK Antibodies on Food Intake & Weight Gain in Zucker Rats", Physiology & Behavior, vol. 34, pp. 277–282, 1985.
Muirhead, "USDA, biotech firm develop compound to get pigs to eat", Feedstuffs, p. 10, May 22, 1989.
Burhol, "Gastric Stimulation by Intravenous Injection of Cholecystokinin and Secretin in Fistula Chickens", Scand. J. Gastroent, pp. 49–53, 1974.
Duke, "Recent Studies on Regulation of Gastric Motility in Turkeys", World's Poultry Science Association Invited Lecture, pp. 1–8, 1991.
Savory et al, "Influence of Vagotomy in Domestic Fowls on Feeding Activity, Food Passage, Digestibility and Satiety Effects of Two Peptides", Physiology & Behavior, vol. 33, pp. 987–944, 1984.
Pekas, "Effect of Cholecystokinin Immunization, Enhanced Food Intake and Growth of Swine on Lean Yield and Carcass Composition", American Institute of Nutrition, pp. 563–567, 1990.
Savory et al, "Are there Hunger and Satiety Factors in the Blood of Domestic Fowls?", Appetite, vol. 8, pp. 101–110, 1987.
Sollenberger, "The New Wonders of Barnyard Biotechnology", The Furrow, Corn Belt Edition, pp. 9–13, Jan.–Feb., 1994.
Pekas et al, "Cholecystokinin Octapeptide Immunization: Effect on Growth of Barrows and Gilts", J. Anim. Sci., vol. 71, pp. 2499–2505, 1993.

Savory et al, "Influence on Intravenous Injections of Cholecystokinin on Gastrointestinal Motility in Turkeys and Domestic Fowls", Biochem. Physiol., vol. 70A, pp. 179–189, 1981.
Gibbs et al, Cholecystokinin Decreases Food Intake in Rats, Journal of Comparative and Physiological Psychology, vol. 84, No. 3, pp. 489–495, 1973.
Trout et al, "Immune, Growth and Carcass Responses of Ram Lambs to Active Immunization Against Desulfated Cholecystokinin (CCK–8)", J. Anim. Sci., vol. 67, pp. 2709–2714, 1989.
Spencer, "Immunization Against Cholecystokinin Decreases Appetite in Lambs", J. Anim. Sci., vol. 70, pp. 3820–3824, 1992.
Pekas et al, "Stimulation of Food Intake and Growth of Swine by Cholecystokinin Immunization", Growth, Development & Aging, vol. 54, pp. 51–56, 1990.
Baile et al, "Hormones and feed intake", Proc. Nutr. Soc., vol. 42, pp. 113–127, 1983.
Walsh, "Gastrin", Gut Peptides: Biochemistry and Physiology, pp. 75–76, 1994.
Scott et al, "Nutrition of the Chicken", Scott & Associates, Second Edition, pp. 435–437., 1976.
Ologhobo et al, "Utilisation of Raw Jackbean (*Canavalia Ensiformis*) and Jackbean Fractions in Diets for Broiler Chicks", British Poultry Science, vol. 34, pp. 323–337, 1993.
Ologhobo et al, "Toxicity of Raw Limabeans (Phaseolus Lunatus L.) and Limabean Fractions for Growing Chicks", British Poultry Science, vol. 34, pp. 505–522, 1993.
Fuller, Jr. "Microwave Treated Whole Soybeans as a Feedstuff in Poultry Diets", a thesis submitted to the Graduate Faculty in Partial Fulfillment of the Requirements for the Degree of Master of Science, Iowa State University, Ames, Iowa, pp. 1–13, 1985.
Evans et al, "Influence of Heat and Supplementation with Methionine on the Nutritive Value of Soybean Protein", J. Nutri., 31, 449, as it appears in Handbook of Nutritive Value of Processed Food, vol. II, Animal Feedstuffs, pp. 327–330, 1946.
McNaughton et al, "Relationships Between Color, Trypsin Inhibitor Contents, and Urease Index of Soybean Meal and Effects on Broiler Performance", Poultry Science, vol. 60, pp. 393–400, 1981.
Herkelman et al, "Effects of Heat Treatment on the Nutritional Value of Conventional and Low Trypsin Inhibitor Soybeans for Chicks", Poultry Science, vol. 72, pp. 1359–1369, 1993.

(List continued on next page.)

*Primary Examiner*—Sheela Huff
*Attorney, Agent, or Firm*—Andrus, Sceales, Starke & Sawall

[57] ABSTRACT

A method of increasing food efficiency in both avians and mammals by using antibodies to gut peptides such as choleocystokinin to elicit a biological response which decreases gastrointestinal motility, reduces satiety or improves feed efficiency.

27 Claims, No Drawings

OTHER PUBLICATIONS

The Merck Index, Eleventh Edition, 1989, pp. 341 and 1352.

"Cholecystokinin", Annals of the New York Academy of Sciences, vol. 713, pp. 12 and 33, 1994.

"Neurotransmitters and Neuromodulators", Gainer and Brownstein, pp. 164–167, 1981.

Gut Peptides, Biochemistry and Physiology, Raven Press, New York (1994).

Morrison et al, Organic Chemistry, 4$^{th}$ Edition, pp. 787, 789, 799, 825–826 (1983).

"Molecular Design of Life", Biochemistry, 3$^{rd}$ Edition, p. 22 (1989).

Biochemicals, Organic Compounds, Diagnostic Reagents, SIGMA product order list (1993).

Savory et al, "Intravenous Injections of Cholecystokinin and Caerulein Suppress Food Intake in Domestic Fowls", Experientia 36, pp. 1191–1193, 1980.

Della–Ferra et al, "Cholecystokinin Antibody Injected in Cerebral Ventricles Stimulates Feeding in Sheep", Science, vol. 212, pp. 687–689, 1981.

Van Wormhoudt et al, "Action de L'inhibiteur trypsique de soja sur la croissance et L'activite des enzymes digestives chez Penaeus japonicus, role eventuel des hormones gastro–intesinales", Oceanis, vol. 12, No. 4, pp. 305–319, 1986.

Inoue et al, "Suppression of Pancreatic Polypeptide and Pancreatic Secretions by Specific Cholecystokinin Antibody in Dogs", Surgical Forum, vol. 34, pp. 216–217, 1983.

McLaughlin et al, Physiology & Behavior vol. 34 p. 277, 1985.

Walsh, Gut Peptides: Biochemistry and Physiology, eds/. Walsh and Dockey, pp. 75–76, 1994.

Baile et al, Proc. Nutr. Soc. vol. 42 p. 113, 1983.

Della–Fera et al Science vol. 212 p. 687, May 1981.

CCK ANTIBODIES USED TO IMPROVE FEED EFFICIENCY

CROSS-REFERENCE TO RELATED APPLICATIONS

This application is a continuation-in-part of U.S. patent application Ser. No. 08/286,376 filed Aug. 5, 1994, now abandoned.

STATEMENT REGARDING FEDERALLY SPONSORED RESEARCH OR DEVELOPMENT

This invention was made with United States government support awarded by the following agencies:

USDA HATCH FUNDS

The United States has certain rights in this invention.

FIELD OF THE INVENTION

This invention relates to eliciting biological response in mammals or poultry either by passive transfer of an antibody or upon feeding an antibody containing substance to the animal. Specifically, this invention relates to increasing food efficiency, decreasing gastrointestinal motility and decreasing satiety in animals and humans by the use of antibodies to choleocystokinin (CCK).

BACKGROUND OF THE INVENTION

The immune system, based on several kinds of specialized blood white cells, is a highly specific defense system that recognizes, eliminates and remembers foreign macromolecules and cells. While functioning properly, it can distinguish between "self" and "non-self" (foreign) materials. For example, it views tumor cells as non-self and hence attacks them, protecting animals against cancer-causing tumor cells as it protects against other invading macromolecules.

An antigen is a foreign substance that when introduced into an animal with a functioning immune system, can elicit a specific immune response such as the one mentioned above. Once activated the immune response involves, among other things, production of antibodies in the circulation system specific to that antigen. There are five distinct classes of antibodies which are also called immunoglobulins. The most abundant is IgG. The other four are IgM, IgA, IgD, and IgE. These antibodies combine with the antigen and act to neutralize or counter the effects of the antigen introduced into the animal. They accomplish this result by binding to the antigen thereby neutralizing it and preventing it from binding to other specific cell receptors.

The immune system can be used not only to fight off pathogenic antigens or harmful foreign molecules, but can be manipulated in order to elicit favorable responses which are not naturally occurring. For example, naturally occurring proteins in an animal can be neutralized via introduction of antibodies specific to that protein thereby neutralizing that protein's normal physiological affect on the animal's system.

There are several ways in which an animal becomes immune responsive. For example, some antibodies are able to traverse the placenta from a mother's circulation to that of her fetus. As a result, the progeny of that mother receives natural immune protection by "inheriting" the mother's own antibodies before birth.

A second way to elicit an immune response is through introduction of an antigen into one animal, resulting in that animal developing specific antibodies to that antigen. These antibodies can then be isolated from the animal and introduced into a second animal resulting in the second animal having antibody that can bind the specific antigen.

BRIEF SUMMARY OF THE INVENTION

This invention pertains to eliciting an immune response in animals and humans in order to increase food efficiency. The antibody used in this invention is an antibody specific to the peptide choleocystokinin (CCK). The choleocystokinin antibody (CCK antibody), upon introduction to the animal, causes an increased efficiency of converting food to body weight gain and through an apparent decreased gastrointestinal motility thereby increasing food efficiency.

The CCK peptide is as follows:

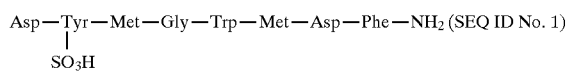
Asp—Tyr—Met—Gly—Trp—Met—Asp—Phe—NH₂ (SEQ ID No. 1)
            |
           SO₃H The CCK peptide can also be in a non-amide form:

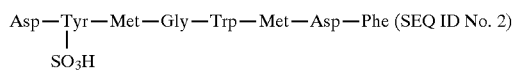
Asp—Tyr—Met—Gly—Trp—Met—Asp—Phe (SEQ ID No. 2)
            |
           SO₃H CCK is an octapeptide that has been shown to negatively affect food intake and thus inhibit growth in both mammals (Gibbs et al, 1973) and birds (Savory and Hodgkiss, 1984). CCK antibodies have been successfully produced endogenously in pigs (Pekas and Trout, 1990; Pekas 1991) and rats (MacLaughlin et al, 1985). In both species, the adverse effects of CCK on food intake and weight gain were prevented by endogenous circulation of CCK antibodies.

The effects of CCK in domestic fowls is well known (Savory et al, 1981). CCK represents a polypeptide hormone which is released when food enters the small intestine. The presence of CCK in the gut mucosa alters gastrointestinal (GI) motility. The gizzard controls the rate in which food travels through the intestine and CCK, which is normally released after a meal is consumed, causes a decrease in gizzard contraction and an increase in intestinal contraction. This results in less time for the absorption of food and nutrients in the intestinal tract. The inventors have found that transferring CCK antibody to poultry increases feed efficiency. In other words, the birds gain more weight per pound of food.

The presence of CCK also alters the willingness to eat. CCK is responsible for what is known as the satiety effect which is a physiological effect that sharply decreases an avian's appetite. If an antibody combines with CCK, CCK is neutralized, the satiety effect is inhibited and adverse effects of endogenous CCK on gastrointestinal motility is averted. Thus, the avian gains more weight per unit of intake. It has not previously been seen that CCK antibodies function in avians or function orally and are actually able to neutralize the negative affects of CCK.

Neuropeptide Y and bombesin have similar physiological effects to CCK on mammalian systems and avian systems. These neuropeptides are also found in the gut and alter feeding behavior.

The effect of CCK antibodies on food efficiency and weight gain can be achieved by (1) passively transferring the CCK antibodies from the dam to offspring, (e.g. by injecting the breeder hen such that the offspring have increase levels of CCK antibody); (2) by feeding a yolk product high in CCK antibody directly to the animal; or (3) injecting a substance high in CCK antibody directly to the animal.

The method in which an immune response is achieved passively involves inoculating a female avian with a specific antigen which results in passively transferring the antibody to the female's offspring. This passive transfer of antibodies to CCK from the dam to the progeny resulting in improved conversion of food into body weight has not previously been seen in the art.

This invention also relates to a specific antibody containing substance produced from the egg of a hen immunized against a selected antigen wherein the substance is mixed with feed and subsequently fed to poultry to elicit altered but improved physiological response. Antibodies to CCK can be produced in laying hens, passed to the yolk, harvested from the yolk or fed as dried yolk, and used as a feed additive for improving feed efficiency in poultry has also not been previously appreciated in the art.

This invention has many advantages. One advantage is that individuals in the commercial meat industry can achieve market weight in livestock or poultry using less time and less feed thereby drastically reducing costs.

A second advantage to the present invention is that the CCK antibodies neutralize CCK but have no known harmful side affects and do not appear to affect meat quality. Also, the cost of utilizing this invention, even on a large scale, is relatively low since only 0.1 to 1 CCK antibody-containing egg is required per eight pounds of feed.

In addition, using the method of feeding the antibody to domesticated animals is relatively low in labor costs since the antibody can simply be mixed with feed and thus, not every individual animal must be injected with the antibody. Also, there is no need to separate or isolate the antibody from the egg since whole egg or yolk can simply be spray dried and fed directly.

Another advantage of this invention is that it counteracts the negative affect of feeding raw soybean meal to poultry or livestock. For example, a typical chick diet contains 40% soybean meal. However, raw soybean meal cannot be fed to poultry because it contains trypsin inhibitor which inhibits the ability of trypsin to digest protein. Therefore, raw soybean meal causes increased levels of CCK with a concurrent decrease in feed efficiency. In order to counter this effect, soybeans must be heat treated in order to be fed to poultry. The typical process for preparing soybean involves heating the beans, extracting the oils and using the remaining meal for chick feed. Specifically, the beans must be heated to at least 121° C. for approximately 20–40 minutes. There are several problems associated with preparing soybeans for poultry feed. One is that the heating process must be performed at an extremely high temperature to ensure destruction of the trypsin inhibition factor. Secondly, heating has a negative impact on the quality of proteins in the soy meal and makes the denatured protein difficult to digest properly. However, the inventors have found that CCK antibodies protect against the negative effects of feeding raw soybeans to fowl.

In addition to soybean, there are a number of other plants that contain trypsin inhibitor, including wheat, barley, lima beans and various legumes. It is predicted that the CCK antibody will also protect against the negative affects of feeding products made from wheat, barley, lima bean or legumes to poultry or livestock.

This invention also has many advantages over what is currently being used in the poultry and livestock industries. Antibiotics are currently used in the commercial animal industry in order to increase food efficiency and weight gain. However, antibiotics leave a drug residue in the animal's tissue. Therefore, the animal must go through "withdrawal time". Withdrawal time is an amount of time sufficient for the antibiotic to clear animal tissues. During withdrawal time, the animal cannot be slaughtered for human consumption. Additionally, any eggs or milk produced cannot be utilized for human use. This precaution is utilized because of the concern that human consumption of milk with traces of penicillin, for example, will cause increase resistance to antibiotics in man, eventually rendering the use of antibiotics to fight bacterial diseases useless.

Secondly, the use of antibiotics over a long period of time can potentially cause an increased number of microorganisms able to infect an animal because these organisms slowly gain resistance due to constant exposure to the antibiotic. Thus, future bacterial diseases will be difficult if not impossible to treat.

CCK also has the same effects of increased GI motility and satiety inhibition in mammals (Pekas and Trout, 1990). It is a well known fact that mammalian species passively transfer antibodies to their progeny as do avians and that mammals respond to CCK autoimmunization as do avians. The dam's antibodies are also identical to those passively transferred to the progeny in avians as well as mammals. Similarly, feeding raw soybean exerts analogous increases in CCK production in mammals as it does in birds (Weller et al, 1990; Chohen et al, 1993; Can J An Sci 73; 401). Therefore, based on the aforementioned facts, the protective effects of actively fed and passively transferred CCK antibodies against satiety and poor feed conversion resulting from CCK observed in avians would also be seen in mammals. Using CCK on various livestock such as cattle and swine would drastically increase their final weight using the same amount of animal meal. Thus the costs to produce an animal of market size is decreased and this would have an enormously beneficial effect on the livestock industry.

The invention would be highly beneficial to humans who are underweight or have problems maintaining their weight. Additionally, individuals with eating disorders would benefit from this invention because their food intake could be controlled.

As previously stated, there are other gastrointestinal peptides or hormones which have an effect on an animal's feeding behavior and digestion. The example of CCK and the method of using CCK antibodies directed toward that peptide in order to prevent CCK's adverse effects suggests that similar responses could be achieved using other antibodies specific to gastrointestinal peptides or hormones. For example, gastrin is involved in signaling acid secretion into the gut and has a trophic action on gastric mucosa leading to hyperplasia. An antibody to gastrin could be used to decrease acid secretion in animals with gastric ulcers or in cases where there is gastric ELC cell carcinoid tumors due to prolonged hypergastrinemia. Gut somatostatin inhibits food intake in fed animals as well as many other gut activities. An antibody to somatostatin could prevent its inhibitory activities. Bombesin stimulates a release of CCK. One could hypothesize that inhibiting bombesin using an antibody specific to bombesin may result in responses similar to antibodies specific to CCK. Neuropeptide Y has been reported to be a stimulus in feeding. It may be possible to inhibit its activity and regulate obesity in animals prone to develop such problems. The biological activity of other peptides which regulate intestinal motility and other functional properties of the intestine could be regulated using the technology described.

In general, by generating antibodies to peptides, hormones, cytokines, etc. that regulate biochemical, metabolic, physiological, and/or behavioral processes, it may be possible to regulate or alter an animal's system to compensate for a physical abnormality or accentuate a normal function.

DETAILED DESCRIPTION OF THE INVENTION

As previously mentioned, there are three modes in eliciting an immune response to CCK in mammals or poultry: passive transfer, active feeding, and active inoculation.

The mode of this invention which relates to passively transferring antibodies involves injecting laying hens with CCK wherein the hens produce antibodies specific to CCK and, as a result, those antibodies are then passively transferred into the egg yolk of eggs laid by the hens. The chick embryo absorbs the CCK antibody during embryonic development. Thereafter, the CCK antibodies become circulating in the hatched chick's bloodstream as well as passed to the gastrointestinal tract.

Either purified CCK or synthesized CCK peptide can be used. Well known means in the art can be used for purifying the CCK peptide such as fractionization, chromatography, precipitation or extraction. However, CCK should be conjugated with a carrier or foreign protein for use as the antigen. CCK alone has a molecular weight less than 1,500 Daltons. In order to invoke an immune response, a molecular weight of at least 10,000 Daltons is required. Therefore, the CCK peptide should be conjugated with a carrier protein with a molecular weight of approximately 8,000 Daltons or more in order for the conjugate to elicit an immune response. Carriers include a wide variety of conventionally known substances but commonly entail bovine gamma globulin or keyhole limpet hemocyanin.

The CCK peptide conjugated to its carrier protein is injected into the target animal with a common adjuvant. The CCK-carrier conjugate can be emulsified in Freund's complete adjuvant, for example. If mammals are the target animals, then subsequent inoculations should consist of incomplete adjuvant.

Another mode of this invention involves orally feeding a CCK antibody containing substance produced from eggs of a CCK vaccinated hen. The CCK antibody containing eggs are prepared and mixed into animal meal. Poultry or mammals which consume this antibody containing meal soon show beneficial response by preventing the satiety effects specific to CCK.

The production of CCK antibody for oral administration can be done by utilizing known technology for producing antibodies in egg yolks. In that process, hens are challenged by injecting them with CCK conjugated to a carrier protein. In response to exposure to the CCK antigen, the eggs laid by these hens contain high levels of CCK antibody in the yolk. Automated systems then separate and spray dry the yolks into a powder. The yolks can alternatively be lyophilized. This standard technique is well established in the art for producing various antibodies for other purposes (e.g. diagnoses, resistance to pathogens, etc.)

Whole eggs may be used and it is therefore not necessary to separate the yolk from the albumen. Typically, 0.1 to 1 CCK containing egg is used per 8 pounds of feed.

Chickens are the most preferable source of eggs but eggs from turkeys, geese, ducks and the like may also be used.

While eggs are the logical source of massive quantities of antibodies, it is possible to collect the antibodies from whole blood, plasma or serum when chickens are processed for meat. In addition, whole blood, plasma or serum from inoculated livestock may be another source of antibodies as well as milk derived from an inoculated cow or goat. Additionally, another source of antibody production is through cell fusion using hybridoma techniques, genetically altered cell cultures or fermentation using recombinant technology.

A third mode of this invention is via inoculation. CCK antibodies can be directly injected into a target animal in order to elicit the desired response of satiety and improved feed conversion.

The target animal receiving the CCK antibody varies greatly. Commercial animals such as livestock, poultry and pelt-animals (e.g. mink, sable, etc.) are ideal candidates. Additionally, humans who have difficulty gaining weight are also considered within the scope of this invention.

PASSIVELY TRANSFERRED CCK ANTIBODIES ON PERFORMANCE OF YOUNG LEGHORN CHICKS

Example 1

Methods

Choleocystokinin (CCK-8) (Fragment 26–33 amide with sulfated tyrosine) was conjugated to keyhole limpet hemocyanin (KLH) using glutaraldehyde and was emulsified with Freund's complete adjuvant (1:1) and injected (100 ug CCK) into 11 Single Comb White Leghorn laying hens. A second injection of the CCK-8 conjugate in Freund's incomplete adjuvant was injected 7 days after primary injection. Another group of control hens which did not receive the CCK injection were also used. Hens (control and CCK injected) were fertilized (artificially using semen collected from New Hampshire roosters). Fertile eggs collected 5 months after the initial injection were used to determine chick performance as a result of passively transferred CCK antibodies. Fifteen chicks hatched from the control hens and 15 chicks hatched from the CCK injected hens were raised in battery brooders on corn-soybean meal based diets for 6 weeks. Body weight gain and feed consumption data were collected.

Results

Chicks from CCK injected hens had improved feed conversion (less feed per pound of gain) which was 14% better than chicks from the control hens. Also, feed intake was increased in CCK birds. The results are shown as Table I.

TABLE I

| Antibody Treatment | 6 Week Gain* | % Change | 6 Week Intake* | % Change | 6 Week Conversion | % Change |
|---|---|---|---|---|---|---|
| Control | 297 | | 745 | | 2.51 | |
| CCK | 352 | +18 | 756 | +1 | 2.15 | −14 |

*Body weight, body wt gain and feed intake are measured in grams.

Example 2

Methods

Eggs from hens immunized with CCK (as shown in Example 1) and from control hens were collected at approximately 10 months after the primary inoculation. Two pens of 13 chicks (representing both the control and CCK immunized hens) were fed a corn-soybean meal based diet to determine if passively transferred CCK antibodies would influence performance as seen in Example 1. Birds were raised for 4 weeks. Body weights and feed consumption were determined.

Results

Feed conversion was improved 2% in chicks from CCK immunized hens when compared to chicks from control hens. The results are shown as Table II.

TABLE II

| Treatment | 4 Week Weight* | % Change | 4 Week Intake* | % Change | 4 Week Conversion | % Change |
|---|---|---|---|---|---|---|
| Control | 158 |  | 383 |  | 2.42 |  |
| CCK | 151 | −4 | 360 | −6 | 2.38 | −2 |

*Body weight, body wt gain and feed intake are measured in grams.

Example 3

Methods

Fertile eggs were collected approximately 8 months after primary inoculation from control and CCK injected hens (immunization as described in Example 1) and used to study the effects of CCK immunization on progeny performance. Two pens of 17 progeny chicks per pen from CCK injected hens and 2 pens of 17 progeny chicks per pen from control hens were raised for 4 weeks. Body weight and feed consumption were measured.

Results

Chicks from CCK injected hens had a 5.2% improvement in feed conversion than chicks from control hens. The results are shown as Table III.

TABLE III

| Treatment | 4 Week Weight* | % Change | 4 Week Intake* | % Change | 4 Week Conversion | % Change |
|---|---|---|---|---|---|---|
| Control | 246 |  | 473 |  | 1.92 |  |
| CCK | 245 | 0 | 447 | −5.5 | 1.82 | −5.2 |

*Body weight, body wt gain and feed intake are measured in grams.

Example 4

Methods

In this study, 2 pens of 15 chicks per pen from CCK immunized hens (as shown in Example 1 and 7 months following the hen's primary inoculation) and 2 pens of 12 chicks per pen from control hens were raised on a corn-soybean meal based diet supplemented with 5% raw soybeans for 3 weeks (raw soybeans were used to stimulate CCK production). Body weight and feed consumption were measured.

Results

Chicks from CCK injected hens had a 10% improvement in feed conversion when compared to chicks from control hens. The results are shown in Table IV.

TABLE IV

| Treatment | 3 Week Weight* | % Change | 3 Week Intake* | % Change | 3 Week Conversion | % Change |
|---|---|---|---|---|---|---|
| Control | 169 |  | 395 |  | 2.34 |  |
| CCK | 161 | −5 | 338 | −14 | 2.10 | −10 |

*Body weight, body wt gain and feed intake are measured in grams.

PROTOCOL FOR THE EFFECTS OF PASSIVELY TRANSFERRED CCK ANTIBODY ON THE PERFORMANCE OF YOUNG BROILER CHICKS

Example 5

Methods

Broiler breeders were immunized with CCK conjugated to KLH using the protocol described in example 1. Since these breeders were maintained on the floor, fertile eggs were produced as a result of natural matings. A total of 10 hens received the CCK immunization (antigen prepared as in example 1 for Leghorns), and 10 hens served as controls. Approximately 21 to 30 days after the primary inoculation, fertile eggs were collected from the control and CCK immunized hens. Seven broiler chicks from the control hens and 7 broiler chicks from the CCK injected hens were hatched and raised in a battery brooder for 3 weeks. Body weight and feed consumption were measured.

Results

Feed conversion was improved 20% and body weight 8% in broiler chicks from CCK immunized hens as compared to broiler chicks from control hens. See Table V for results.

TABLE V

| Treatment | 3 Week Weight* | % Change | 3 Week Intake* | % Change | 3 Week Conversion | % Change |
|---|---|---|---|---|---|---|
| Control | 396 |  | 604 |  | 1.53 |  |
| CCK | 427 | +8 | 526 | −13 | 1.23 | −20 |

*Body weight, body wt gain and feed intake are measured in grams.

Example 6

Methods

Two pens of 6 chicks from CCK immunized broiler breeders 7 weeks after the primary inoculation as in Example 5 and 2 pens of 6 chicks per pen from the control hens were hatched and raised to 3 weeks of age on a standard broiler type diet. Body weight and feed consumption were measured.

Results

Broiler chicks from CCK immunized hens gained 16% more body weight and converted food 12.5% more efficiently than chicks from the control hens. See Table VI for results.

TABLE VI

| Treatment | 3 Week Weight* | % Change | 3 Week Intake* | % Change | 3 Week Conversion | % Change |
|---|---|---|---|---|---|---|
| Control | 380 |  | 547 |  | 1.44 |  |
| CCK | 441 | +16 | 547 | 0 | 1.26 | −12.5 |

*Body weight, body wt gain and feed intake are measured in grams.

FEEDING EGG YOLKS FROM CONTROL AND CCK IMMUNIZED HENS

Example 7

Methods

Control or CCK immunized hens were prepared as described in Example 1. Eggs from control and CCK immunized hens were collected after at least 21 days following the primary inoculation. Yolks were collected from the eggs (albumen was discarded) and control or anti-CCK yolks were separately pooled, frozen, then freeze dried. The control and CCK antibody dried yolks were then ground and added to a standard corn-soybean based diet at 0.5, 1.0, or 5% of the diet (weight by weight) creating 3 control treatments and 3 anti-CCK treatments. Each dietary treatment was fed to two pens of 9 leghorn type chicks for 4 weeks. Body weight gains, feed consumption, and feed conversion were determined.

Results

As the level of anti-CCK egg yolk increased, body weight gain increased relative to those fed the control egg yolk. At each level of anti-CCK egg yolk feeding, feed conversion was improved over those fed the control yolk. See Table VII for results.

TABLE VII

| Treatment | % Fed | Feed Intake* | Feed Conversion |
|---|---|---|---|
| | | 0–4 weeks of age | |
| Control Yolk | .5 | 692 | 2.88 |
| CCK Yolk | .5 | 680 | 2.50 |
| Control Yolk | 1.0 | 656 | 2.39 |
| CCK Yolk | 1.0 | 649 | 2.29 |
| Control Yolk | 5 | 712 | 2.55 |
| CCK Yolk | 5 | 772 | 2.49 |

*Body weight, body wt gain and feed intake are measured in grams.

EFFECTS OF PASSIVELY TRANSFERRING CCK ANTIBODY IN PREVENTING THE NEGATIVE EFFECTS OF FEEDING RAW SOYBEANS ON FEED CONVERSION

Example 8

Methods

Immunized hens (Leghorns) were prepared as described in Example 1. Hens were artificially fertilized and eggs were collected and incubated. Chicks (Single Comb White Leghorn X New Hampshire) were hatched and 2 pens of 12 chicks were assigned to each of 4 treatments. The treatments included 2 sources of chicks (progeny from control or CCK immunized hens) factorially arranged with 2 dietary treatments (5 or 10% raw soybeans at the expense of diet). The chicks were fed the diets for 4 weeks and body weight and feed consumption were measured.

Results

Chicks from CCK immunized hens had improved feed conversion (11% to 19%) when compared to their respective control diets. As the level of raw soybeans increased in the diet, feed conversion was poorer (12% poorer in the control progeny, but only 6% poorer in the progeny chicks from the CCK injected hens). See Table VIII for results.

TABLE VIII

| % Raw Soybean | Passive CCK Antibody | 4 Week Weight* | % Change | 4 Week Conversion | % Change |
|---|---|---|---|---|---|
| 5 | − | 202 | | 2.63 | |
| 5 | + | 205 | +1.5 | 2.34 | −11 |
| 10 | − | 192 | | 2.94 | |
| 10 | + | 197 | +2.6 | 2.48 | −19 |

*Body weight, body wt gain and feed intake are measured in grams.

FEEDING ANTI-PEPTIDES TO BROILER CHICKS

Example 9

Summary: Broiler chicks were purchased from an outside vendor and fed various antibodies to peptides of GI tract to establish any type of phenomena that may occur related to body weight and/or feed conversion.

| Animals: | |
|---|---|
| Species: | Broiler Chicken |
| Strain: | Avian X Avian |
| Source: | Northern Hatcheries (Beaver Dam, WI) |
| Vaccinations: | Mareks, Gumboro, New Castle/Bronchitis, AE |
| Sex: | Male |
| Number of each | 32 |

FEEDING PROTOCAL (Treatments)

| Diets: | | | |
|---|---|---|---|
| | | | (g/kg) |
| Peptide Identification | Lot Number | | 0.5 |
| bGG Control | N3 Control | E-457A | X |
| Bombesin | P6 | P6-32995 | X |
| Motilin | P7 | P7-32995 | X |
| Neuropeptide Y | P8 | P8-32995 | X |

| Trial Set-Up | | | | | |
|---|---|---|---|---|---|
| Number of Pens | Birds per Pen | Floor | Battery | Pens per Treatment | Birds per Treatment |
| 8 | 4 | | X | 2 | 8 |

| Results: | | | | |
|---|---|---|---|---|
| Treatment | 3 Week Body Wt (g) | 0–3 Body Wt Gain (g) | 0–3 Feed/Bird | 0–3 Feed/Gain |
| Control | 543 | 503 | 786 | 1.56 |
| Bombesin | 530 | 490 | 774 | 1.58 |
| Motilin | 554 | 494 | 795 | 1.61 |
| Neuropeptide Y | 537 | 495 | 711 | 1.44 |

The above data show that chicks fed bombesin, motilin and neuropeptide Y all show weight gain comparable to control. In particular, the use of neuropeptide Y results in substantially the same weight gain over time as control, but with significantly less feed than control.

FEEDING AVENO AND NEUROPEPTIDE Y TO BROILER CHICKS

Example 10

Summary: Broiler chicks were hatched from UW stock and fed yolk from hens injected with Aveno or Neuropeptide Y when compared to control powder from N3 series.

| Animals: | |
|---|---|
| Species: | Broiler Chicken |
| Strain: | Petersen X Arbor Acre |
| Source: | UW Stock |
| Vaccinations: | None |
| Sex: | Mixed |
| Number of each | 175 |

FEEDING PROTOCAL (Treatments)

| Diets | | | | | |
|---|---|---|---|---|---|
| | | | (g of egg yolk antibody powder per kg feed) | | |
| | Peptide Identification | Lot Number | 0.25 | 0.5 | 1.0 |
| bGG Control | N3 Control | E457A | | X | |
| Reverse Bravo | P10 | P10-61695 | | X | X |
| Aveno | P11 | P11-61695 | | X | X |
| Neuropeptide Y | P8 | P8-32995 | X | X | |

| Trial Set-Up | | | | | |
|---|---|---|---|---|---|
| Number of Pens | Birds per Pen | Floor | Battery | Pens per Treatment | Birds per Treatment |
| 35 | 5 | | X | 5 | 25 |

| Results: Feed Conversions | |
|---|---|
| Treatment | 1–3 Feed/Gain |
| Control (0.5) | 1.63 |
| Aveno (0.5) | |
| Aveno (1.0) | |
| Reverse (0.5) | |
| Reverse (1.0) | |
| Peptide 8 (0.25) | 1.58 |
| Peptide 8 (0.5) | 1.71 |

Note: This trial started when the birds were one week of age, therefore we will not have a 0–2 feed/gain.

| Treatment (g yolk/kg feed) | 3 Wk Weight (gain) (g) |
|---|---|
| Control | 418 (328) |
| Aveno (0.5) | |
| Aveno (1.5) | |
| Reverse (0.5) | |
| Reverse (1.0) | |
| Peptide 8 (0.25) | 475 (379) |
| Peptide 8 (0.5) | 442 (349) |

These data show that feeding neuropeptide Y (Peptide 8) resulted in chicks having significantly greater weight gain versus control chicks.

FEEDING ANTI-BRAVO ANTIBODIES TO BROILER CHICKS

Example 11

Summary: Broiler chicks were hatched at the UW poultry research lab and fed Anti-Bravo from a specified lot of Gutteridge product (G111S) to monitor a dose response similar to these seen with the N-series products. Also monitor Peptide 8 to see if it has similar properties to Bravo.

| Animals: | |
|---|---|
| Species: | Broiler Chicken |
| Strain: | Petersen X Arbor Acre |
| Source: | UW stock |
| Vaccinations: | none |
| Sex: | Mixed |
| Number of each | 75 |

| Fertility Information: | | | | |
|---|---|---|---|---|
| Treatment | Infertile | Early Deads | No Hatch | Hatched |
| Control Bravo | 66 | 24 | 35 | 415 |

FEEDING PROTOCOL (Treatments)

| Diets: | | |
|---|---|---|
| | | (g/kg) |
| | Lot Number | 0.25 |
| N3 Control | E-457A | X |
| Bravo (G111S) | A2-61695 | X |
| Peptide 8 (Neuro Y) | 32995 | X |

| Trial Set-up: (Birds per Rx = 25) | | | | | |
|---|---|---|---|---|---|
| Number of Pens | Birds per Pen | Floor | Battery | Passive | Control (bGG) |
| 15 | 5 | | X | | 75 |

| Feed: | | | |
|---|---|---|---|
| Rx | Control 0.25 | G111S 0.25 | Peptide 8 0.25 |
| 1 | X | | |
| 2 | | X | |
| 3 | | | X |

| Results: Feed Conversion | | | |
|---|---|---|---|
| RX | 0–1 Feed/Gain | 0–2 Feed/Gain | 0–3 Feed/Gain |
| Control | 1.66 | 1.60 | 1.96 |
| G. Bravo (0.25) | 1.67 (−1) | 1.62 (−2) | 1.89 (7) |
| Peptide 8 | 1.63 | 1.61 | 1.83 (13) |

| | Body Weights (gains): | | |
|---|---|---|---|
| Rx | 1 wk (gain) (g) | 2 wk (gain) (g) | 3 wk (gain) (g) |
| Control | 111 (70) | 247 (205) | 432 (390) |
| G. Bravo (0.25) | 102 (61) | 231 (190) | 407 (366) |
| Peptide 8 | 110 (69) | 262 (221) | 465 (423) |

Note: These suppressions in weight gain for Bravo are probably due to the high titer of the product used.

These data show that feeding neuropeptide Y (Peptide 8) resulted in chicks having significantly greater weight gain versus control.

FEEDING PEPTIDES 6, 7 & 8 TO BROILER CHICKS

Example 12

Summary: To determine if there is an effect in improving feed conversion when feeding any of these peptides to broiler chicks.

| Animals: | |
|---|---|
| Species: | Broiler Chicken |
| Strain: | Petersen X Arbor Acre |
| Source: | UW Stock (Controls Only) |
| Vaccinations: | NONE |
| Sex: | Mixed |
| Number of each | 100 |

FEEDING PROTOCOL (Treatments)

| | Diets: | |
|---|---|---|
| | | (g/kg) |
| Treatments | Lot Number | 0.25 |
| Control | M57A | X |
| Peptide 6 (Bombesin) | P32995 | X |
| Peptide 7 (Motilin) | P32995 | X |
| Peptide 8 (Neuropeptide Y) | P32995 | X |

| | | Trial Set-up: | | |
|---|---|---|---|---|
| Number of Pens | Birds per Pen | Floor Battery | Pens per Treatment | Birds per Treatment |
| 20 | 5 | X | 5 | 25 |

| | Results: | | |
|---|---|---|---|
| Treatment | 0–1 Feed/Gain | 0–2 Feed/Gain | 0–3 Feed/Gain |
| Control | 1.51 | 1.68 | 1.71 |
| Peptide 6 | 1.48 | 1.58 | 1.64 |
| Peptide 7 | 1.63 | 1.59 | 1.63 |
| Peptide 8 | 1.38 | 1.55 | 1.69 |

| | Body Weights (grams): | | |
|---|---|---|---|
| Treatment | 1 Week | 2 Week | 3 Week |
| Control | 119 (72) | 258 (211) | 480 (433) |
| Peptide 6 | 115 (70) | 274 (229) | 509 (463) |
| Peptide 7 | 116 (71) | 272 (226) | 505 (460) |
| Peptide 8 | 124 (78) | 296 (250) | 562 (516) |

Note Chicks were hatched from BgG hens instead of purchased.

These data show that bombesin (Peptide 6), motilin (Peptide 7) and neuropeptide Y (Peptide 8) all significantly increased body weights of chicks versus control. In each case, the peptide resulted in chicks with greater body weight for the same amount of feed fed to the chicks.

FEEDING PEPTIDES 6, 7 AND 8 TO RATS

Example 13

Summary: Rats purchased from Harlan Sprague Dawley were fed antibodies to GI tract peptides from a specified lot to establish the appropriate dose level to increase or decrease consumption after 72 hours.

| Animals: | |
|---|---|
| Species: | Rat |
| Strain: | Sprague Dawley |
| Source: | Harlan Sprague Dawley Madison, WI |
| Vaccinations: | none |
| Sex: | Male |
| Number of each | 41 |

FEEDING PROTOCOL (Treatments)

| | Diets: | | |
|---|---|---|---|
| | | | (g/kg) |
| | Lot Number | 0.25 | 0.50 |
| bGG Control | E457A | X | |
| Peptide 6 | 32995 | X | X |
| Peptide 7 | 32995 | X | X |
| Peptide 8 | 32995 | X | X |

| | | Trial Set-up: | | |
|---|---|---|---|---|
| Number of Pens | Rat per Cage | Floor | Cage | Cages per Treatment |
| 41 | 1 | | X | 6 |

| | Results: | |
|---|---|---|
| Treatment (g yolk/kg feed) | 0–3 Day Consumption (g) | 0–3 Feed/Kg of Body Wt |
| Control | 76.16 | 205.343 |
| Peptide 6 (0.25) | 71.2 | 187.86 |
| Peptide 7 (0.25) | 71.2 | 182.85 |
| Peptide 8 (0.25) | 71 | 186.63 |
| Peptide 6 (0.5) | 72.5 | 193.67 |

-continued

| Treatment (g yolk/kg feed) | Results: 0-3 Day Consumption (g) | 0-3 Feed/Kg of Body Wt |
|---|---|---|
| Peptide 7 (0.5) | 70.8 | 189.25 |
| Peptide 8 (0.5) | 72 | 189.86 |

FEEDING BRAVO TO PIGS

Example 14

Summary: Pigs were fed Bravo to establish bioactivity relating to feeding and growth behavior.

| | | | | Results: | | |
|---|---|---|---|---|---|---|
| Treatment* | (lbs) 2 week wt | (kg) 0-2 gain | (kg) adg | (kg) 0-2 Feed consumption | 0-2 feed/kg body wt. | 0-2 feed/ gain |
| Control | 66.3 | 10.4 | 0.741 | 19.31 | 0.638 | 1.870 |
| 0.25 | 63.8 | 9.8 | 0.703 | 19.19 | 0.663 | 1.959 |
| 0.75 | 64.7 | 10.7 | 0.763 | 19.43 | 0.661 | 1.821 |
| 2.5 | 68.3 | 11.1 | 0.790 | 20.66 | 0.660 | 1.878 |

*grams of egg yolk antibody powder/kg feed

---

We claim:

1. A method of modulating feeding behavior in animals, comprising the step of feeding an antibody to a gut peptide to an animal by oral administration in order to alter a physiological effect of said peptide relating to feeding or growth behavior.

2. The method of claim 1 wherein said gut peptide is choleocystokinin.

3. The method of claim 2 wherein said choleocystokinin is purified choleocystokinin peptide.

4. The method of claim 2 wherein said choleocystokinin is synthetic choleocystokinin peptide.

5. The method of claim 2 wherein said choleocystokinin is sulfated.

6. The method of claim 2 wherein said choleocystokinin is an amide.

7. The method of claim 1 wherein said gut peptide is bombesin.

8. The method of claim 1 wherein said gut peptide is neuropeptide Y.

9. The method of claim 1 wherein said gut peptide is gastrin.

10. The method of claim 1 wherein said gut peptide is somatostatin.

11. The method of claim 1 wherein said animal is an avian.

12. The method of claim 4 wherein said avian is a chicken.

13. The method of claim 1 wherein said animal is a mammal.

14. The method of claim 13 wherein said mammal is selected from the group consisting of a porcine, a bovid, an ovine, a caprine, a rodentia and a homo sapien.

15. A method of modulating feeding behavior in animals, comprising the steps of:

immunizing a producer animal with a gut peptide so that said producer animal produces an antibody to said gut peptide;

isolating a substance containing said gut peptide antibody from said producer animal; and feeding said substance containing said gut peptide antibody to an animal by oral administration.

16. The method of claim 15 wherein said gut peptide is choleocystokinin.

17. The method of claim 15 wherein said gut peptide is bombesin.

18. The method of claim 15 wherein said gut peptide is neuropeptide Y.

19. The method of claim 15 wherein said gut peptide is gastrin.

20. The method of claim 15 wherein said gut peptide is somatostatin.

21. The method of claim 16 wherein said choleocystokinin is conjugated to a carrier protein.

22. The method of claim 21 wherein said carrier protein is keyhole limpet hemocyanin.

23. The method of claim 21 wherein said carrier protein is bovine gamma globulin.

24. The method of claim 15 wherein said substance containing said gut peptide antibody is selected from the group consisting of milk, whole egg and egg yolk.

25. The method of claim 15 wherein said substance containing said gut peptide antibody is selected from the group consisting of whole blood, blood serum and blood plasma.

26. The method of claim 15 further including the steps of separating the gut peptide antibody from said substance, and thereafter feeding said gut peptide antibody to said animal.

27. The method of claim 15 wherein said animal is selected from the group consisting of an avian, a porcine, a bovine, an ovine, a caprine, a rodentia and a homo sapien.

* * * * *

UNITED STATES PATENT AND TRADEMARK OFFICE
CERTIFICATE OF CORRECTION

PATENT NO. : 5,827,517
DATED : October 27, 1998
INVENTOR(S) : Mark E. Cook et al It is certified that error appears in the above-indentified patent and that said Letters Patent is hereby corrected as shown below:

Claim 12, col. 17, line 34          Delete the number "4" and substitute therefor ---11---

Signed and Sealed this

Fourteenth Day of December, 1999

Attest:

Q. TODD DICKINSON

Attesting Officer          Acting Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 8
      ( B ) TYPE: amino acid
      ( D ) TOPOLOGY: Linear ( i i ) MOLECULE TYPE:
      ( A ) DESCRIPTION: peptide ( i i i ) HYPOTHETICAL: no ( i v ) ANTI-SENSE: no ( i x ) FEATURE:
      ( A ) NAME/KEY: Choleocystokinin
      ( D ) OTHER INFORMATION: Tyr 2 has an "-SO3H"group
          attached; Phe 8 has an "-NH2"
          attached; Causes satiety ( x i ) SEQUENCE DESCRIPTION: SEQ ID NO: 1:

Asp  Tyr  Met  Gly  Trp  Met  Asp  Phe
      1                    5

( 2 ) INFORMATION FOR SEQ ID NO:2:

( i ) SEQUENCE CHARACTERISTICS:
      ( A ) LENGTH: 8
      ( B ) TYPE: amino acid
      ( D ) TOPOLOGY: Linear ( i i ) MOLECULE TYPE:
      ( A ) DESCRIPTION: peptide ( i i i ) HYPOTHETICAL: no ( i v ) ANTI-SENSE: no ( i x ) FEATURE:
      ( A ) NAME/KEY: Choleocystokinin
      ( D ) OTHER INFORMATION: Tyr 2 has an "-SO3H"
          group attached; Causes satiety ( x i ) SEQUENCE DESCRIPTION: SEQ ID NO: 2:

```
Asp  Tyr  Met  Gly  Trp  Met  Asp  Phe
1                    5
```